US006440970B1

(12) United States Patent
Clark et al.

(10) Patent No.: US 6,440,970 B1
(45) Date of Patent: Aug. 27, 2002

(54) PHARMACEUTICAL COMPOSITIONS AND METHODS FOR USE

(75) Inventors: Thomas Jeffrey Clark, High Point; Gary Maurice Dull, Lewisville; Dwo Lynm, Winston-Salem; Lan Miao, Winston-Salem; Craig Harrison Miller, Winston-Salem; Jeffrey Daniel Schmitt, Winston-Salem, all of NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/578,768

(22) Filed: May 25, 2000

(51) Int. Cl.$^7$ .................. C07D 487/08; C07D 471/08; C07D 519/00; A61K 31/395; A61P 25/00

(52) U.S. Cl. .................. 514/249; 544/349; 544/295; 544/238; 514/252.02; 514/275

(58) Field of Search .................. 544/349, 295, 544/238; 514/249, 275, 252.02

(56) References Cited

U.S. PATENT DOCUMENTS

| 5,478,939 A | * 12/1995 | Trybulski et al. ............ 544/336 |
| 5,726,189 A | 3/1998 | London et al. .............. 514/339 |
| 5,853,696 A | 12/1998 | Elmaleh et al. ............ 424/1.85 |
| 5,969,144 A | 10/1999 | London et al. .......... 546/276.7 |

FOREIGN PATENT DOCUMENTS

| WO | WO 97/40049 | * 10/1997 |
| WO | 00 44755 | 8/2000 |
| WO | 00 66586 | 11/2000 |

OTHER PUBLICATIONS

CAS printout for Smith et al.*
CAS printout for Arrowsmith et al.*
CAS printout for Czollner et al.*
Villemagne et al., "Nicotine and Related Compounds as PET and SPECT Ligands," Neuronal Nicotinic Receptors: Pharmacology and Therapeutic Opportunities, 1998, pp 235–250.
Sihver et al., "In Vitro Evaluation of $^{11}$C–Labeled (S)–Nicotine, (S)–3–Methyl–5–(1–Methyl–2–Pyrrolidinyl)isoxazole, and (R,S)–1–Methyl–2–(3–Pyridyl)azetidine as Nicotinic Receptor Ligands for Positron Emission Tomography Studies," J. Neurochem. vol. 71, No. 4, 1998, pp. 1750–1760.
Musachio et al., "[$^{125/123}$I]IPH: A Radioiodinated Analog of Epibatidine for In Vivo Studies of Nicotinic Acetylcholine Receptors," Synapse, vol. 26, 1997, pp. 392–399.
Nordberg et al., "Uptake and regional distribution of (+)–R–and (–)–(S)–N–[methyl–$^{11}$C]–nicotine in the brains of Rhesus monkey. An attempt to study nicotinic receptors in vivo," J. Neural Transm [P–D Sect] vol. 1, 1989, pp. 195–205.

Horti et al., "Synthesis and Evaluation of N–[$^{11}$C]Methylated Analogues of Epibatidine as Tracers for Positron Emission Tomographic Studies of Nicotinic Acetylcholine Receptors," Journal of Medicinal Chemistry, vol. 41, No. 22, 1998, pp. 4199–4206.
Dollé et al., "Synthesis and Nicotinic Acetylocholine Receptor in Vivo Binding Properties of 2–Fluoro–3–[2(S)–2–azetidinlymethoxy]pyridine: A New Positron Emission Tomography Ligand for Nicotinic Receptors," J. Med. Chem, vol. 42, 1999, pp. 2251–2259.
Horti et al., "Synthesis of a Radiotracer for Studying Nicotinic Acetylcholine Receptors: (+/–)–exo–2–(2–[18F]fluoro–5–pyridyl)–7–azabicyclo[2.2.1]heptane," Journal of Labelled Compounds and Radiopharmaceuticals, vol. XXXVIII, No. 4, pp. 356–365.
Oya et al., "A New Single–Photon Emission Computer Tomography Imaging Agent for Serotonin Transporters: [$^{123}$I]IDAM, 5–Iodo–2–((2–((dimethylamino)methyl)–phenyl)thio)benzyl Alcohol," Journal of Medicinal Chemistry, vol. 42, No. 3, Feb. 11, 1999, pp. 333–335.
Liang et al., "Synthesis and Nicotinic Acetylcholine Receptor Binding Properties of exo–2–(2'–Fluoro–5'–pyridinyl)–7–azabicyclo–[2.2.1]heptane: A New Positron Emission Tomography Ligand for Nicotinic Receptors," J. Med. Chem, vol. 40, 1997, pp. 2293–2295.
Malpass et al., "Synthesis of 5–and 6–chloropyridyl–substituted 2–azabicyclo[2.2.1]heptanes; novel epibatidine isomers," Tetrahedron Letters, vol. 40, 1999, pp. 1419–1422.
Musachio et al., "5–[1–125/123] Iodo–3(2(S)–Azetidinylmethoxy)Pyridine, A Radioiodinated Analog of A–85380 for In Vivo Studies of Central Nicotinic Acetylcholine Receptors," Life Sciences, vol. 62, No. 22, 1998, pp. PL351–357.
International Search Report for PCT/US01/16941.

* cited by examiner

Primary Examiner—Mukund J. Shah
Assistant Examiner—Hong Liu
(74) Attorney, Agent, or Firm—Womble Carlyle Sandridge & Rice, PLLC

(57) ABSTRACT

The present invention relates to diazabicyclic compounds, and preferably N-aryl diazabicyclic compounds. Of particular interest are 2-pyridyl diazabicyclic compounds, such as (1S,4S)-2-(3-pyridyl)-2,5-diazabicyclo[2.2.1]heptane. Other exemplary compounds of the present invention include: (1S,4S)-2-(5-(4-methoxyphenoxy)-3-pyridyl)-2,5-diazabicyclo[2.2.1]heptane, (1S,4S)-2-(5-pyrimidinyl)-2,5-diazabicyclo[2.2.1]heptane and (1S,4S)-2-(6-chloro-3-pyridazinyl)-2,5-diazabicyclo[2.2.1]heptane. The present invention also relates to prodrug derivatives of the compounds of the present invention.

10 Claims, No Drawings

PHARMACEUTICAL COMPOSITIONS AND METHODS FOR USE

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). Confirmatory reports and additional recent studies have included the modulation in the CNS of, glutamate, nitric oxide, GABA, takykinins, cytokines and peptides (reviewed in Brioni J. D., Decker M. W., Sullivan J. P., and Arneric S. P. (1997) The pharmacology of (−)-nicotine and novel cholinergic channel modulators In Advances in Pharmacology, Vol 37, pp 153–214, eds August J T, Anders M W, Murad F, and Coyle J T, Academic Press.). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221: 91–96 (1982) and Hamon, *Trends in Pharmacol. Res.* 15:36.

Various nicotinic compounds have been reported as being useful for treating a wide variety of conditions and disorders. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, PCT WO 96/40682, and U.S. Pat. No. 5,583,140 to Bencherif et al., U.S. Pat. No. 5,597,919 to Dull et al. U.S. Pat. No. 5,604,231 to Smith et al. and U.S. Pat. No. 5,852,041 to Cosford et al. Nicotinic compounds are reported as being particularly useful for treating a wide variety of Central Nervous System (CNS) disorders. Indeed, a wide variety of compounds have been reported to have therapeutic properties. See, U.S. Pat. No. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), micro-infarct dementia, AIDS-related dementia, Creutzfeld-jakob disease, Pick's disease, Parkinsonism including Parkinson's disease, progressive supranuclear palsy, Huntington's chorea, tardive dyskinesia, hyperkinesia, mania, attention deficit disorder, anxiety, dyslexia, schizophrenia, depression, obsessive compulsive disorders and Tourette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to effect the functioning of the CNS, but which compound when employed in an amount sufficient to effect the functioning of the CNS, does not significantly effect those receptor subtypes which have the potential to induce undesirable side effects (e.g., appreciable activity at cardiovascular and skeletal muscle sites).

SUMMARY OF THE INVENTION

The present invention relates to diazabicyclic compounds, and preferably N-aryl diazabicyclic compounds. Of particular interest are 2-pyridyl diazabicyclic compounds, such as (1S,4S)-2-(3-pyridyl)-2,5-diazabicyclo[2.2.1]heptane. Other exemplary compounds of the present invention include: (1S,4S)-2-(5-(4-methoxyphenoxy)-3-pyridyl)-2,5-diazabicyclo[2.2.1]heptane, (1S,4S)-2-(5-pyrimidinyl)-2,5-diazabicyclo[2.2.1]heptane and (1S,4S)-2-(6-chloro-3-pyridazinyl)-2,5-diazabicyclo[2.2.1]heptane. The present invention also relates to prodrug derivatives of the compounds of the present invention.

The present invention also relates to methods for the prevention or treatment of a wide variety of conditions or disorders, and particularly those disorders characterized by dysfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and/(ii) modulate neurotransmitter secretion, and hence prevent and suppress the symptoms associated with those diseases. In addition, the compounds are expected to have the potential to (i) alter the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastrointestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds having a diazabicyclic ring. The structure can be represented by the formula:

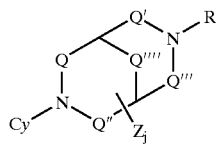

In the structure, Q is $(CH_2)_u$, Q' is $(CH_2)_v$, Q'' is $(CH_2)_w$, Q''' is $(CH_2)_x$, Q'''' is $(CH_2)_y$, where u,v,w and x are individually 0, 1, 2, 3 or 4, preferably 0 or 1, and y is 1 or 2. R is hydrogen, or lower alkyl, preferably hydrogen. In addition, the values of u, v, w, x and y are selected such that the resulting diazabicyclic ring contains 7, 8 or 9 members, preferably 7 members.

In the structure, Cy represents a suitable 6 member aromatic ring, and exemplary ring systems are set forth hereinafter, Z represents suitable a non-hydrogen substituent group, and exemplary groups are set forth hereinafter. In addition, j is an integer from 0 to 10, preferably 0 or 1.

Representative compounds of the present invention include the following:

where Cy=

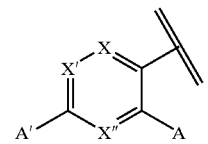

Each of X, X' and X" are individually nitrogen, nitrogen bonded to oxygen (e.g., an N-oxide or N-O functionality) or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., Chem. Rev. 91:165 (1991). When any of X, X' and X" are carbon bonded to a substituent species, those substituent species typically have a sigma m value between about −0.3 and about 0.75, frequently between about −0.25 and about 0.6; and each sigma m value individually can be 0 or not equal to zero. In addition, A, A', and Z individually are either hydrogen or suitable non-hydrogen substituent species; and typically those substituent species have a sigma m value between about −0.3 and about 0.75, frequently between about −0.25 and about 0.6; and each sigma m value individually can be 0 or not equal to zero. Most preferably, at least one of X' and X" is nitrogen. However, for certain compounds, it is also preferable that X and X' both are nitrogen. Preferably, 1 or 2 of X, X' and X" are nitrogen or nitrogen bonded to oxygen. In addition, it is highly preferred that not more than one of X, X' and X" be nitrogen bonded to oxygen; and it is preferred that if one of those species is nitrogen bonded to oxygen, that species is X". Typically, X' is CH, CBr, CSR', CNR' or COR', where R' preferably is benzyl, phenyl, substituted phenyl, methyl, ethyl, isopropyl, isobutyl, tertiary butyl or cycloalkyl (e.g., cyclopropyl, cyclobutyl, cyclopentyl, cyclohexyl or cycloheptyl, phenyl or mono-, di-, or tri-substituted phenyl with substituents the same as A defined hereafter). Most preferably, X" is nitrogen. For certain other preferred compounds X" is CNR'R", COR' or $CNO_2$, typically $CNH_2$, $CNHCH_3$ or $CN(CH_3)_2$, with C—$NH_2$ being preferred. In certain preferred circumstances, both X' and X" are nitrogen. Typically, X is carbon bonded to a substituent species, and it is typical that X is carbon bonded to a substituent species such as hydrogen. For certain other preferred compounds where X" is carbon bonded to a substituent species such as hydrogen, X and X' are both nitrogen. Adjacent substituents of X, X', A', X" and A (when adjacent X, X' and X" each are carbon bonded to a respective substituent component) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities.

The substituents of either X, X' or X" (when each respective X, X' and X" is carbon), the substituents A, A' and Z, and the substituents attached to six member heteroaromatic ring representatives of unit Cy can include alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo (e.g., F, Cl, Br, or I), —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_q$OR', —OC(=O)R', —(CR'R")$_q$OCH$_2$C$_2$R', —(CR'R")$_q$C(=O)R', —O(CR'R")$_q$C(=O)R', —C$_2$(CR'R")$_q$O R', —(CR'R")$_q$NR'R", —OC(=O)NR'R" and —NR'C(=O)OR' where R' and R" are individually hydrogen or lower alkyl (e.g., straight chain or branched alkyl including C$_1$–C$_8$, preferably C$_1$–C$_5$, such as methyl, ethyl, or isopropyl), an aromatic group-containing species or a substituted aromatic group-containing species, and q is an integer from 1 to 6. R' and R" can form a cycloalkyl functionality. Representative aromatic group-containing species include any of the foregoing can be suitably substituted with at least one substituent group, such as alkyl, halo, or amino substituents). Other representative aromatic ring systems are set forth in Gibson et al., *J. Med. Chem.* 39:4065 (1996). The substituents of X, X' and X", the substituents A and A', and the substituents attached to six member heteroaromatic ring representatives of unit Cy individually can include hydrogen.

As employed herein, "alkyl" refers to straight chain or branched alkyl radicals including C$_1$–C$_8$, preferably C$_1$–C$_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including C$_1$–C$_8$, preferably C$_1$–C$_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

Of particular interest are compounds of the formula set forth hereinbefore wherein preferably u,v,w,and x are preferably 0 or 1, y is preferably 1 or 2 and j is 0; preferably Cy is 3-pyridyl (unsubstituted or substituted in the 5 and/or 6 position(s) with any of the aforementioned substituents), 5-pyrimidinyl (unsubstituted or substituted in the 2 position with any of the aforementioned substituents); preferably R is hydrogen or lower alkyl.

Representative compounds of the present invention include the following:

(1R,4R)-2-(3-pyridyl)-2,5-diazabicyclo[2.2.1]heptane
(1S,4S)-2-(3-pyridyl)-2,5-diazabicyclo[2.2.1]heptane
(1R,4R)-2-(3-pyridyl)-5-methyl-2,5-diazabicyclo[2.2.1]heptane
(1S,4S)-2-(3-pyridyl)-5-methyl-2,5-diazabicyclo[2.2.1]heptane
(1R,4R)-2-(5-hydroxy-3-pyridyl)-2,5-diazabicyclo[2.2.1]heptane
(1S,4S)-2-(5-hydroxy-3-pyridyl)-2,5-diazabicyclo[2.2.1]heptane
(1R,4R)-2-(5-methoxy-3-pyridyl)-2,5-diazabicyclo[2.2.1]heptane
(1S,4S)-2-(5-methoxy-3-pyridyl)-2,5-diazabicyclo[2.2.1]heptane
(1R,4R)-2-(5-ethoxy-3-pyridyl)-2,5-diazabicyclo[2.2.1]heptane
(1S,4S)-2-(5-ethoxy-3-pyridyl)-2,5-diazabicyclo[2.2.1]heptane
(1R,4R)-2-(5-isopropoxy-3-pyridyl)-2,5-diazabicyclo[2.2.1]heptane
(1S,4S)-2-(5-isopropoxy-3-pyridyl)-2,5-diazabicyclo[2.2.1]heptane
(1R,4R)-2-(5-isobutoxy-3-pyridyl)-2,5-diazabicyclo[2.2.1]heptane
(1S,4S)-2-(5-isobutoxy-3-pyridyl)-2,5-diazabicyclo[2.2.1]heptane
(1R,4R)-2-(5-phenoxy-3-pyridyl)-2,5-diazabicyclo[2.2.1]heptane
(1S,4S)-2-(5-phenoxy-3-pyridyl)-2,5diazabicyclo[2.2.1]heptane
(1R,4R)-2-(5-benzyloxy-3-pyridyl)-2,5-diazabicyclo[2.2.1]heptane
(1S,4S)-2-(5-benzyloxy-3-pyridyl)-2,5diazabicyclo[2.2.1]heptane
(1R,4R)-2-(5-methoxymethyl-3-pyridyl)-2,5-diazabicyclo[2.2.1]heptane
(1S,4S)-2-(5-methoxymethyl-3-pyridyl)-2,5-diazabicyclo[2.2.1]heptane
(1R,4R)-2-(5-(4-piperidinyloxy)-3-pyridyl)-2,5-diazabicyclo[2.2.1]heptane
(1S,4S)-2-(5-(4-piperidinyloxy)-3-pyridyl)-2,5-diazabicyclo[2.2.1]heptane
(1R,4R)-2-(5-(4-(N-trifluoroacetylpiperidinyl)oxy)-3-pyridyl)-2,5-diazabicyclo[2.2.1]heptane
(1S,4S)-2-(5-(4-(N-trifluoroacetylpiperidinyl)oxy)-3-pyridyl)-2,5-diazabicyclo[2.2.1]heptane
(1R,4R)-2-(5-phenyl-3-pyridyl)-2,5-diazabicyclo[2.2.1]heptane
(1S,4S)-2-(5-phenyl-3-pyridyl)-2,5-diazabicyclo[2.2.1]heptane
(1R,4R)-2-(5-bromo-3-pyridyl)-2,5-diazabicyclo[2.2.1]heptane
(1S,4S)-2-(5-bromo-3-pyridyl)-2,5-diazabicyclo[2.2.1]heptane
(1R,4R)-2-(5-fluoro-3-pyridyl)-2,5-diazabicyclo[2.2.1]heptane
(1S,4S)-2-(5-fluoro-3-pyridyl)-2,5-diazabicyclo[2.2.1]heptane
(1R,4R)-2-(5-chloro-3-pyridyl)-2,5-diazabicyclo[2.2.1]heptane
(1S,4S)-2-(5-chloro-3-pyridyl)-2,5-diazabicyclo[2.2.1]heptane
(1R,4R)-2-(5-iodo-3-pyridyl)-2,5-diazabicyclo[2.2.1]heptane (1S,4S)-2-(5-iodo-3-pyridyl)-2,5-diazabicyclo[2.2.1]
  heptane
(1R,4R)-2-(5-pyrimidinyl)-2,5-diazabicyclo[2.2.1]heptane
(1S,4RS)-2-(5-pyrimidinyl)-2,5-diazabicyclo[2.2.1]heptane
(1R,4R)-2-(6-chloro-3-pyridazinyl)-2,5-diazabicyclo[2.2.1]
  heptane
(1S,4S)-2-(6-chloro-3-pyridazinyl)-2,5-diazabicyclo[2.2.1]
  heptane
(1R,4R)-2-(6-methoxy-3-pyridazinyl)-2,5-diazabicyclo
  [2.2.1]heptane
(1S,4S)-2-(6-methoxy-3-pyridazinyl)-2,5-diazabicyclo
  [2.2.1]heptane
(1R,4R)-2-(6-methoxy-3-pyridazinyl)-2,5-diazabicyclo
  [2.2.1]heptane
(1S,4S)-2-(6-methoxy-3-pyridazinyl)-2,5-diazabicyclo
  [2.2.1]heptane The following compounds also are representative compounds of the present invention:

3-(3-pyridyl)-3,6-diazabicyclo[3.2.1]octane
3-(3-pyridyl)-6-methyl-3,6-diazabicyclo[3.2.1]octane
3-(5-hydroxy-3-pyridyl)-3,6-diazabicyclo[3.2.1]octane
3-(5-methoxy-3-pyridyl)-3,6-diazabicyclo[3.2.1]octane
3-(5-ethoxy-3-pyridyl)-3,6-diazabicyclo[3.2.1]octane
3-(5-isopropoxy-3-pyridyl)-3,6-diazabicyclo[3.2.1]octane
3-(5-isobutoxy-3-pyridyl)-3,6-diazabicyclo[3.2.1]octane
3-(5-phenoxy-3-pyridyl)-3,6-diazabicyclo[3.2.1]octane
3-(5-benzyloxy-3-pyridyl)-3,6-diazabicyclo[3.2.1]octane
3-(5-methoxymethyl-3-pyridyl)-3,6-diazabicyclo[3.2.1]
  octane
3-(5-(4-piperidinyloxy)-3-pyridyl)-3,6-diazabicyclo[3.2.1]
  octane
3-(5-phenyl-3-pyridyl)-3,6-diazabicyclo[3.2.1]octane
3-(5-bromo-3-pyridyl)-3,6-diazabicyclo[3.2.1]octane
3-(5-fluoro-3-pyridyl)-3,6-diazabicyclo[3.2.1]octane
3-(5-chloro-3-pyridyl)-3,6-diazabicyclo[3.2.1]octane
3-(5-iodo-3-pyridyl)-3,6-diazabicyclo[3.2.1]octane
3-(5-pyrimidinyl)-3,6-diazabicyclo[3.2.1]octane
3-(6-chloro-3-pyridazinyl)-3,6-diazabicyclo[3.2.1]octane
3-(6-methoxy-3-pyridazinyl)-3,6-diazabicyclo[3.2.1]octane
3-(3-pyridyl)-3,6-diazabicyclo[3.2.2]nonane
3-(3-pyridyl)-6-methyl-3,6-diazabicyclo[3.2.2]nonane
3-(5-hydroxy-3-pyridyl)-3,6-diazabicyclo[3.2.2]nonane
3-(5-methoxy-3-pyridyl)-3,6-diazabicyclo[3.2.2]nonane
3-(5-ethoxy-3-pyridyl)-3,6diazabicyclo[3.2.2]nonane
3-(5-isopropoxy-3-pyridyl)-3,6-diazabicyclo[3.2.2]nonane
3-(5-isobutoxy-3-pyridyl)-3,6-diazabicyclo[3.2.2]nonane
3-(5-phenoxy-3-pyridyl)-3,6-diazabicyclo[3.2.2]nonane
3-(5-benzyloxy-3-pyridyl)-3,6-diazabicyclo[3.2.2]nonane
3-(5-methoxymethyl-3-pyridyl)-3,6-diazabicyclo[3.2.2]
  nonane
3-(5-(4-piperidinyloxy)-3-pyridyl)-3,6-diazabicyclo[3.2.2]
  nonane
3-(5-phenyl-3-pyridyl)-3,6-diazabicyclo[3.2.2]nonane
3-(5-bromo-3-pyridyl)-3,6-diazabicyclo[3.2.2]nonane
3-(5-fluoro-3-pyridyl)-3,6-diazabicyclo[3.2.2]nonane
3-(5-chloro -3-pyridyl)-3,6-diazabicyclo[3.2.2]nonane
3-(5-iodo-3-pyridyl)-3,6-diazabicyclo[3.2.2]nonane
3-(5-pyrimidinyl)-3,6-diazabicyclo[3.2.2]nonane
3-(6-chloro-3-pyridazinyl)-3,6-diazabicyclo[3.2.2]nonane
3-(6-methoxy-3-pyridazinyl)-3,6-diazabicyclo[3.2.2]
  nonane
6-(3-pyridyl)-3,6-diazabicyclo[3.2.1]octane
6-(3-pyridyl)-3-methyl-3,6-diazabicyclo[3.2.1]octane
6-(5-methoxy-3-pyridyl)-3,6-diazabicyclo[3.2.1]octane
6-(5-ethoxy-3-pyridyl)-3,6-diazabicyclo[3.2.1]octane
6-(5-isopropoxy-3-pyridyl)-3,6-diazabicyclo[3.2.1]octane
6-(5-isobutoxy-3-pyridyl)-3,6-diazabicyclo[3.2.1]octane
6-(5-phenoxy-3-pyridyl)-3,6-diazabicyclo[3.2. 1]octane
6-(5-benzyloxy-3-pyridyl)-3,6-diazabicyclo[3.2.1]octane
6-(5-methoxymethyl-3-pyridyl)-3,6-diazabicyclo[3.2.1]
  octane
6-(5-(4-piperidinyloxy)-3-pyridyl)-3,6-diazabicyclo[3.2.1]
  octane
6-(5-phenyl-3-pyridyl)-3,6-diazabicyclo[3.2.1]octane
6-(5-bromo-3-pyridyl)-3,6-diazabicyclo[3.2.1]octane
6-(5-fluoro-3-pyridyl)-3,6-diazabicyclo[3.2.1]octane
6-(5-chloro-3-pyridyl)-3,6-diazabicyclo[3.2.1]octane
6-(5-iodo-3-pyridyl)-3,6-diazabicyclo[3.2.1]octane
6-(5-pyrimidinyl)-3,6-diazabicyclo[3.2.1]octane
6-(6-chloro-3-pyridazinyl)-3,6-diazabicyclo[3.2.1]octane
6-(6-methoxy-3-pyridazinyl)-3,6-diazabicyclo[3.2.1]octane The following compounds also are representative compounds of the present invention:

3-(3-pyridyl)-3,7-diazabicyclo[3.3.1]nonane
3-(3-pyridyl)-7-methyl-3,7-diazabicyclo[3.3.1]nonane
3-(5-methoxy-3-pyridyl)-3,7-diazabicyclo[3.3.1]nonane
3-(5-ethoxy-3-pyridyl)-3,7-diazabicyclo[3.3.1]nonane
3-(5-isopropoxy-3-pyridyl)-3,7-diazabicyclo[3.3.1]nonane
3-(5-isobutoxy-3-pyridyl)-3,7-diazabicyclo[3.3.1]nonane
3-(5-phenoxy-3-pyridyl)-3,7-diazabicyclo[3.3.1]nonane
3-(5-benzyloxy-3-pyridyl)-3,7-diazabicyclo[3.3.1]nonane
3-(5-methoxymethyl-3-pyridyl)-3,7-diazabicyclo[3.3.1]
  nonane
3-(5-(4-piperidinyloxy)-3-pyridyl)-3,7-diazabicyclo[3.2.1]
  octane
3-(5-phenyl-3-pyridyl)-3,7-diazabicyclo[3.3.1]nonane
3-(5-bromo-3-pyridyl)-3,7-diazabicyclo[3.3.1]nonane
3-(5-fluoro-3-pyridyl)-3,7-diazabicyclo[3.3.1]nonane
3-(5-chloro-3-pyridyl)-3,7-diazabicyclo[3.3.1]nonane
3-(5-iodo-3-pyridyl)-3,7-diazabicyclo[3.3.1]nonane
3-(5-pyrimidinyl)-3,7-diazabicyclo[3.3.1]nonane
3-(6-chloro-3-pyridazinyl)-3,7-diazabicyclo[3.3.1]nonane
3-(6-methoxy-3-pyridazinyl)-3,7-diazabicyclo[3.3.1]
  nonane.

The manner in which N-aryl diazabicyclic compounds of the present invention are synthetically produced can vary. Commercially available (Aldrich Chemical) (1S,4S)-N-(tert-butoxycarbonyl)-2,5-diazabicyclo[2.2.1]heptane can be coupled with a variety of aromatic halides and heteroaromatic halides using palladium catalysis. See Yang et al. *J. Organomet. Chem.* 576: 125–146 (1999) and Wolfe et al. *Acc. Chem. Res.* 31:805–818 (1998) and Hartwig et al., *J. Org. Chem.* 64: 5575–5580 (1999). For example, treatment of 3,5-dibromopyridine with (1S,4S)-N-(tert-butoxycarbonyl)-2,5-diazabicyclo[2.2.1]heptane in the presence of a catalytic amount of tris(dibenzylideneacetone)dipalladium(0) and 2,2'-bis(diphenylphosphino)-1,1'-binapthyl and sodium tert-butoxide in toluene provides (1S,4S)-5-(tert-butoxycarbonyl)-2-(5-bromo-3-pyridyl)-2,5-diazabicyclo[2.2.1]heptane. The N-tert-butoxycarbonyl protecting group is readily removed in the presence of acid to provide (1S,4S)-2-(5-bromo-3-pyridyl)-2,5-diazabicyclo[2.2.1]heptane. Use of the other enantiomer, (1R,4R)-N-(tert-butoxycarbonyl)-2,5-diazabicyclo[2.2.1]heptane, in the palladium catalyzed coupling will lead to (1R,4R)-2-(5-bromo-3-pyridyl)-2,5-diazabicyclo[2.2.1]heptane. Both the (1S,4S) and the (1R,4R) enantiomers of the N-(tert-butoxycarbonyl)-2,5-diazabicyclo[2.2.1]heptane can be synthesized from hydroxyproline isomers as described in U.S. Pat. Nos. 5,095,121 and 5,196,548 to T. Braish and D. Fox and by T. Braish and D. Fox in *J. Org. Chem.* 55: 1694–1687 (1990). Also reported in these references are the syntheses of the N-benzyl derivatives of (1S,4S)- and (1R,4R)-2,5-diazabicyclo[2.2.1]heptane. Coupling of these diazabicycles with 3,5-dibromopyridine, as described above, would generate the corresponding enantiomeric 5-benzyl-2-(5-bromo-3-pyridyl)-2,5-diazabicyclo[2.2.1]heptanes. Likewise, coupling with 3-bromopyridine would produce the enantiomeric 5-benzyl-2-(3-pyridyl)-2,5-diazabicyclo[2.2.1]heptanes.

A suitably protected derivative of either of 2-(5-bromo-3-pyridyl)-2,5-diazabicyclo[2.2.1]heptane enantiomer can be elaborated to give a number of compounds possessing substituents at the C-5 position of the pyridine. For example, 5-benzyl-2-(5-bromo-3-pyridyl)-2,5-diazabicyclo[2.2.1] heptane can be converted into the corresponding 5-aminosubstituted compound by the general method of C. Zwart et al., *Recueil Trav. Chim. Pays-Bas* 74: 1062–1069 (1955), in which the bromo compound is heated with aqueous ammonia in the presence of a copper catalyst. 5-Alkylamino substituted compounds can be prepared in a similar manner. 5-Ethynyl-substituted compounds can be prepared from the 5-bromo compound by palladium catalyzed coupling using 2-methyl-3-butyn-2-ol, followed by base (sodium hydride) catalyzed removal of the acetone unit, according to the general techniques described in N. D. P. Cosford et al., *J. Med. Chem.* 39: 3235–3237 (1996). The 5-ethynyl analogs can be converted into the corresponding 5-ethenyl, and subsequently to the corresponding 5-ethyl analogs by successive catalytic hydrogenation reactions (which would also remove the benzyl protecting group from the diazabicycle). The 5-azido substituted analogs can be prepared from the 5-bromo compound by reaction with lithium azide in N,N-dimethylformamide. 5-Alkylthio substituted analogs can be prepared from the 5-bromo compound by reaction with an appropriate sodium alkylmercaptide (sodium alkanethiolate), using techniques known to those skilled in the art of organic synthesis.

A number of other analogs, bearing substituents in the 5 position of the pyridine ring, can be synthesized from 5-benzyl-2-(5-amino-3-pyridyl)-2,5-diazabicyclo[2.2.1] heptane (the synthesis of which is described above) via the 5-diazonium salt intermediate. Either enantiomer of the 5-amino compound may be utilized. Among the other 5-substituted analogs that can be produced from 5-diazonium salt intermediates are: 5-hydroxy analogs, 5-alkoxy analogs, 5-fluoro analogs, 5-chloro analogs, 5-bromo analogs, 5-iodo analogs, 5-cyano analogs, and 5-mercapto analogs. These compounds can be synthesized using the general techniques set forth in C. Zwart et al., supra. For example, 5-hydroxy substituted analogs can be prepared from the reaction of the corresponding 5-diazonium salt intermediates with water. 5-Alkoxy analogs can be made from the reaction of the diazonium salts with alcohols. 5-Fluoro substituted analogs can be prepared from the reaction of the 5-diazonium salt intermediates with fluoroboric acid. 5-Chloro substituted analogs can be prepared from the reaction of the 5-amino compounds with sodium nitrite and hydrochloric acid in the presence of copper chloride. 5-Cyano substituted analogs can be prepared from the reaction of the corresponding 5-diazonium salt intermediates with potassium copper cyanide. Appropriate 5-diazonium salt intermediates can also be used for the synthesis of mercapto substituted analogs using the general techniques described in J. M. Hoffman et al.,*J. Med. Chem.* 36: 953–966 (1993). The 5mercapto substituted analogs can in turn be converted to the 5-alkylthio substituted analogs by reaction with sodium hydride and an appropriate alkyl bromide. 5-Acylamido analogs of the aforementioned compounds can be prepared by reaction of the corresponding 5-amino compounds with an appropriate acid anhydride or acid chloride using techniques known to those skilled in the art of organic synthesis.

5-Hydroxy substituted analogs of the aforementioned compounds can be used to prepare corresponding 5-alkanoyloxy substituted compounds by reaction with the appropriate acid, acid chloride, or acid anhydride. 5-Cyano substituted analogs of the aforementioned compounds can be hydrolyzed to afford the corresponding 5-carboxamido substituted compounds. Further hydrolysis results in formation of the corresponding 5-carboxylic acid substituted analogs. Reduction of the 5-cyano substituted analogs with lithium aluminum hydride yields the corresponding 5-aminomethyl analogs. 5-Acyl substituted analogs can be prepared from corresponding 5-carboxylic acid substituted analogs by reaction with an appropriate alkyl lithium using techniques known to those skilled in the art.

5-Carboxylic acid substituted analogs of the aforementioned compounds can be converted to the corresponding esters by reaction with an appropriate alcohol and acid catalyst. Compounds with an ester group at the 5-pyridyl position can be reduced with sodium borohydride or lithium aluminum hydride to produce the corresponding 5-hydroxymethyl substituted analogs. These analogs in turn can be converted to compounds bearing an ether moiety at the 5-pyridyl position by reaction with sodium hydride and an appropriate alkyl halide, using conventional techniques. Alternatively, the 5-hydroxymethyl substituted analogs can be reacted with tosyl chloride to provide the corresponding 5-tosyloxymethyl analogs. The 5-carboxylic acid substituted analogs can also be converted to the corresponding 5-alkylaminoacyl analogs by reaction with an appropriate alkylamine and thionyl chloride.

5-Tosyloxymethyl substituted analogs of the aforementioned compounds can be converted to the corresponding 5-methyl substituted compounds by reduction with lithium aluminum hydride. 5-Tosyloxymethyl substituted analogs of the aforementioned compounds can also be used to produce 5-alkyl substituted compounds via reaction with an alkyllithium. 5-Hydroxy substituted analogs of the aforementioned compounds can be used to prepare 5-N-alkylcarbamoyloxy substituted compounds by reaction with N-alkylisocyanates. 5-Amino substituted analogs of the aforementioned compounds can be used to prepare 5-N-alkoxycarboxamido substituted compounds by reaction with alkyl chloroformate esters, using techniques known to those skilled in the art of organic synthesis.

Chemistries analogous to those described hereinbefore for the preparation of 5-substituted (pyridine) analogs of diazabicyclic compounds, can be devised for the synthesis of analogs bearing substituents in the 2, 4, and 6 positions of the pyridine ring. For example, a number of 2-, 4-, and 6-aminopyridyl diazabicyclic compounds can be converted to the corresponding diazonium salt intermediates, which can be transformed to a variety of compounds with substituents at the 2, 4, and 6 positions of the pyridine ring as was described for the 5-substituted analogs above. The requisite 2-, 4-, and 6-aminopyridyl diazabicycles are available via the Chichibabin reaction of unsubstituted pyridyl diazabicycles (e.g., 5-benzyl-2-(3-pyridyl)-2,5-diazabicyclo[2.2.1] heptane, described previously). Similar reactions are described in *Chemistry of Heterocyclic Compounds, Volume* 14, part 3, pp.3–5 (Interscience Publishers, 1962) and by B.

Lahti, et al. *J. Med. Chem.* 42: 2227–2234 (1999). After the desired pyridine ring functional group manipulation has been accomplished, the benzyl protecting group can be removed from the diazabicycle using hydrogenation conditions.

In an alternative approach to the synthesis of pyridine-substituted pyridyl diazabicyclic compounds, 3,5-dibromopyridine can be converted into the corresponding 3-bromo-5-alkoxy- and 3-bromo-5-aryloxypyridines by the action of sodium alkoxides or sodium aryloxides. Procedures such as those described by D. L. Comins et al., *J. Org. Chem.* 55: 69–73 (1990) and H. J. den Hertog et al., *Recueil Trav. Chim. Pays-Bas* 74: 1171–1178 (1955), are used. This is exemplified by the preparation 2-(5-(4-methoxyphenoxy)-3-pyridyl)-2,5-diazabicyclo[2.2.1]heptane. Reaction of 3,5-dibromopyridine with sodium 4-methoxyphenoxide in N,N-dimethylformamide gives 3-bromo-5-(4-methoxyphenoxy) pyridine. Coupling of 3-bromo-5-(4-methoxyphenoxy) pyridine with (1S,4S)-N-(tert-butoxycarbonyl)-2,5-diazabicyclo[2.2.1]heptane in the presence of a catalytic amount of tris(dibenzylideneacetone)dipalladium(0) and 2,2'-bis(diphenylphosphino)-1,1'-binapthyl and sodium tert-butoxide in toluene provides (1S,4S)-2-(5-(4-methoxyphenoxy)-3-pyridyl)-5-(tert-butoxycarbonyl)-2,5-diazabicyclo[2.2.1]heptane. Removal of the N-tert-butoxycarbonyl group, using trifluoroacetic acid, produces (1S,4S)-2-(5-(4-methoxyphenoxy)-3-pyridyl)-2,5-diazabicyclo[2.2.1]heptane.

Other aryl halides undergo the palladium catalyzed coupling reaction described previously. Thus (1S,4S)-2-(5-pyrimidinyl)-2,5-diazabicyclo[2.2.1]heptane is prepared in a similar manner from 5-bromopyrimidine and (1S,4S)-N-(tert-butoxycarbonyl)-2,5-diazabicyclo[2.2.1]heptane followed by deprotection of the resulting intermediate. (1S,4S)-2-(6-chloro-3-pyridazinyl)-2,5-diazabicyclo[2.2.1] heptane is synthesized similarly from 3,6-dichloropyridazine and (1S,4S)-N-(tert-butoxycarbonyl)-2,5-diazabicyclo[2.2.1]heptane followed by deprotection of the resulting intermediate. This technology is especially applicable in cases (like 3-bromopyridine, 3,5-dibromopyridine, and 5-bromopyrimidine) where the aromatic ring is not activated toward nucleophilic aromatic substitution.

The present invention also relates to the use of other diazabicyclic systems in palladium catalyzed coupling reactions with aryl halides. The procedures described by Old et al., *J. Am. Chem. Soc.* 120: 9722–9723 (1998) and Hartwig et al., *J. Org. Chem.* 64: 5575–5580 (1999) are typical of the conditions used for the coupling. For example, coupling of 3-bromopyridine with 6-carboethoxy-3,6-diazabicyclo[3.2.2]nonane under palladium catalysis will provide 3-(3-pyridyl)-6-carboethoxy-3,6-diazabicyclo[3.2.2]nonane. Hydrolysis of the carboethoxy protecting group using sodium hydroxide/ethylene glycol/water or HBr in acetic acid will lead to 3-(3-pyridyl)-3,6-diazabicyclo[3.2.2] nonane. 6-Carboethoxy-3,6-diazabicyclo[3.2.2]nonane can be produced from 3-benzyl-6-carboethoxy-3,6-diazabicyclo[3.2.2]nonane by hydrogenation in the presence of palladium on carbon. The synthesis of the requisite 3-benzyl-6-carboethoxy-3,6-diazabicyclo[3.2.2]nonane is described by A. Fray et al., *J.Org. Chem.* 53: 896–899 (1988) and in European Patent Application No. 88305925.5, filed Jun. 28, 1988 (Publication No. 0297858A2). Other appropriately substituted aryl halides (e.g., 3,5-dibromopyridine and 5-bromopyrimidine) can be coupled similarly and subsequently transformed into 3-aryl-3,6-diazabicyclo[3.2.2] nonanes.

The 3,6-diazabicyclo[3.2.2]nonane ring system can also be coupled to aryl halides at the 6 position nitrogen atom, producing 6-aryl-3,6-diazabicyclo[3.2.2]nonanes which are isomeric to the 3-aryl-3,6-diazabicyclo[3.2.2]nonanes described previously. Thus, the aforementioned 3-benzyl-6-carboethoxy-3,6-diazabicyclo[3.2.2]nonane can be hydrolyzed to 3-benzyl-3,6-diazabicyclo[3.2.2]nonane, which can subsequently be coupled to an aryl halide in a palladium catalyzed reaction. The 6-aryl-3-benzyl-3,6-diazabicyclo [3.2.2]nonane product can then be hydrogenated to give a 6-aryl-3,6-diazabicyclo[3.2.2]nonane.

Another example of a diazabicyclic analog which can be incorporated into compounds of the present invention is 3,6-diazabicyclo[3.2.1]octane. For instance, the synthesis of both 3-methyl-3,6-diazabicyclo[3.2.1]octane and 6-methyl-3,6-diazabicyclo[3.2.1]octane are described in European Patent Application No. 88305925.5, issued Jun. 28, 1988 (Publication No. 0297858A2). Either of these amines can be coupled with 3-bromopyridine, in a palladium catalyzed process, to give isomeric products, 3-methyl-6-(3-pyridyl)-3,6-diazabicyclo[3.2.1]octane and 6-methyl-3-(3-pyridyl)-3,6-diazabicyclo[3.2.1]octane. The use of other appropriately substituted aryl halides in the coupling reaction will lead to other N-aryl 3,6-diazabicyclo[3.2.1]octane products.

Yet another diazabicycle that is illustrative of the present invention is the 3,7-diazabicyclo[3.3.1]nonane ring system. Thus 3,7-dibenzyl-3,7-diazabicyclo[3.3.1]nonan-8-one, which is readily prepared by double Mannich reaction of N-benzyl4-piperidone with formaldehyde and benzylamine (see Garrison et al., *J. Org. Chem.* 58: 7670–7678 (1993)), can be converted into 3,7-dibenzyl-3,7-diazabicyclo[3.3.1] nonane by either of several deoxygenation reactions. For instance, Wolff-Kishner reduction, using procedures similar to those described by Berlin et al., *Organic Preparations and Proceedings Int.* 31: 413–421 (1999) or the tosylhydrazone method described by L. Caglioti, *Org. Syn.* Coll. Vol. 6: 62–63 (1988), will convert the ketone into the corresponding alkane. Removal of the benzyl groups can then be accomplished by hydrogenation over palladium on carbon. The hydrogenation product of 3,7-diazabicyclo[3.3.1]nonane, can be coupled directly with an aryl halide (such as 3-bromopyridine) under conditions in which the diazabicycle is used in excess, to minimize the production of 3,7-diaryl-3,7-diazabicyclo[3.3.1]nonane. Alternatively, reacting an excess of the 3,7-diazabicyclo[3.3.1]nonane with di-tert-butyl-dicarbonate will provide the monoprotected diazabicycle, 3-(tert-butoxycarbonyl)-3,7-diazabicyclo [3.3.1]nonane, which can subsequently be coupled (palladium catalysis) and deprotected (trifluoroacetic acid) as described previously.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae which are set forth hereinbefore. The present invention relates to a pharmaceutical composition incorporating a compound selected from the general formulae which are set forth hereinbefore. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al., the disclosures of which are incorporated herein by reference in their entirety.

Compounds of the present invention are useful for treating those types of conditions and disorders for which other types of nicotinic compounds have been proposed as therapeutics. See, for example, Williams et al. *DN&P* 7(4):205–227 (1994), Arneric et al., *CNS Drug Rev.* 1(1) :1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597, 919 to Dull et al., and U.S. Pat. No. 5,604,231 to Smith et al the disclosures of which are incorporated herein by reference in their entirety. Compounds of the present invention can be used as analgesics, to treat ulcerative colitis, inflammatory and auto-immune diseases (e.g., arthritis, cholangitis, stomatitis, pouchitis, viral pneumonitis), to treat a variety of neurodegenerative diseases, and to treat convulsions such as those that are symptomatic of epilepsy. CNS disorders which can be treated in accordance with the present invention include presenile dementia (early onset Alzheimer's disease), senile dementia (dementia of the Alzheimer's type), HIV-dementia, multiple cerebral infarcts, Parkinsonism including Parkinson's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome. Compounds of the present invention also can be used to treat conditions such as syphillis and Creutzfeld-jakob disease. The compounds of the present invention also can be appropriately synthesized and used as or within pharmaceutical compositions that are used as diagnostic probes.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids, vitamins, minerals and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 5 mg/kg of patient weight.

Often, the compounds of the present invention are administered in an amount from less than about 1 mg/kg patent weight, and usually less than about 100 ug/kg of patient weight, but frequently between about 10 ug to less than 100 ug/kg of patient weight. For compounds of the present invention that do not induce effects on muscle type nicotinic receptors at low concentrations, the effective dose is less than 5 mg/kg of patient weight; and often such compounds are administered in an amount from 50 ug to less than 5 mg/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about −0.5, often are greater than about 0, and frequently are greater than about 0.5. The log P values of such typical compounds generally are less than about 3, often are less than about 2, and frequently are less than about 1. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause activation of, nicotinic dopaminergic receptors of the brain of the patient. As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of certain compounds are less than about 100 uM, often are less than about 10 uM and frequently are less than about 5 uM; and of preferred compounds generally are less than about 2.5 uM, sometimes are less than about 1 uM, and can be less than about 100 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively activating neurotransmitter secretion from nerve ending preparations (i.e., synaptosomes). As such, these compounds have the ability to activate relevant neurons to release or secrete acetylcholine, dopamine, and other neurotransmitters. Generally, typical compounds useful in carrying out the present invention provide for the activation of dopamine secretion in amounts of at least one third, typically at least about 10 times less, frequently at least about 100 times less, and sometimes at least about 1,000 times less, than those required for activation of muscle-type nicotinic receptors. Certain compounds of the present invention can provide secretion of dopamine in an amount which is comparable to that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder, is essentially ineffective in eliciting activation of certain ganglia-type nicotinic receptors at concentration higher than 5 times, preferably higher than 100 times, and more preferably higher than 1,000 times, than those required for activation of dopamine release. This selectivity of certain compounds of the present invention against those ganglia-type receptors responsible for cardiovascular side effects is demonstrated by a lack of the ability of those compounds to activate nicotinic function of adrenal chromaffin tissue at concentrations greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, an amelioration to some degree of the reoccurrence of CNS disorders. However, such effective amounts of those compounds are not sufficient to elicit any appreciable side effects, as demonstrated by increased effects relating to skeletal muscle. As such, administration of certain compounds of the present invention provides a therapeutic window in which treatment of certain CNS disorders is provided, and certain side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than ⅕, and often less than 1/10 that amount sufficient to cause certain side effects to any significant degree.

The pharmaceutical compositions of the present invention can be employed to prevent or treat certain other conditions, diseases and disorders. Exemplary of such diseases and disorders include inflammatory bowel disease, pouchitis, acute cholangitis, aphteous stomatitis, arthritis (e.g., rheumatoid arthritis and osteartritis), neurodegenerative diseases, cachexia secondary to infection (e.g., as occurs in AIDS, AIDS related complex and neoplasia), as well as those indications set forth in PCT WO 98/25619. The pharmaceutical compositions of the present invention can be employed in order to ameliorate may of the symptoms associated with those conditions, diseases and disorders. Thus, pharmaceutical compositions of the present invention can be used in treating genetic diseases and disorders, in treating autoimmune disorders such as lupus, as anti-infectious agents (e.g, for treating bacterial, fungal and viral infections, as well as the effects of other types of toxins such as sepsis), as anti-inflammatory agents (e.g., for treating acute cholangitis, aphteous stomatitis, asthma, and ulcerative colitis), and as inhibitors of cytokines release (e.g., as is desirable in the treatment of cachexia, inflammation, neurodegenerative diseases, viral infection, and neoplasia), The compounds of the present invention can also be used as adjunct therapy in combination with existing therapies in the management of the aforementioned types of diseases and disorders. In such situations, administration preferably is such that the active ingredients of the pharmaceutical formulation act to optimize effects upon abnormal cytokine production, while minimizing effects upon receptor subtypes such as those that are associated with muscle and ganglia. Administration preferably is such that active ingredients interact with regions where cytokine production is affected or occurs. For the treatment of such conditions or disorders, compounds of the present invention are very potent (i.e., affect cytokine production and/or secretion at very low concentrations), and are very efficacious (i.e., significantly inhibit cytokine production and/or secretion to a relatively high degree).

Effective doses are most preferably at very low concentrations, where maximal effects are observed to occur. Concentrations, determined as the amount of compound per volume of relevant tissue, typically provide a measure of the degree to which that compound affects cytokine production. Typically, the effective dose of such compounds generally requires administering the compound in an amount of much less than 100 ug/kg of patient weight, and even less than 10 u/kg of patient weight. The foregoing effective doses typically represent the amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 1, often does not exceed about 0.75, often does not exceed about 0.5, frequently does not exceed about 0.25 mg/24 hr./patient. In addition, administration of the effective dose is such that the concentration of the compound within the plasma of the patient normally does not exceed 500 pg/ml, often does not exceed 300 pg/ml, and frequently does not exceed 100 pg/ml. When employed in such a manner, compounds of the present invention are dose dependent, and as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The following examples are provided to illustrate the present invention, and should not be construed as limiting the scope thereof. In these examples, all parts and percentages are by weight, unless otherwise noted. Reaction yields are reported in mole percentages.

EXAMPLES

Examples

Assays

Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., Biochem, Pharmacol. 22:3099 (1973).

Determination of Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported $EC_{50}$ values are expressed in nM, and $E_{max}$ values represent the amount released relative to (S)-(−)-nicotine on a percentage basis.

Neurotransmitter Release from Brain Synaptosomes

Neurotransmitter release was measured using techniques similar to those previously published (Bencherif M, et al. JPET 279: 1413–1421, 1996).

Rat brain synaptosomes were prepared as follows: Female Sprague Dawley rats (100–200 g) were killed by decapitation after anesthesia with 70% $CO_2$. Brains are dissected, and hippocampus, striatum, and thalamus isolated, and homogenized in 0.32 M sucrose containing 5 mM HEPES pH 7.4 using a glass/glass homogenizer. The tissue was then centrifuged for 1000×g for 10 minutes and the pellet discarded. The supernatant was centrifuged at 12000×g for 20 minutes. The resultant pellet was re-suspended in perfusion buffer (128 mM NaCl, 1.2 mM $KH_2PO_4$, 2.4 mM KCl, 3.2 mM $CaCl_2$, 1.2 mM $MgSO_4$, 25 mM HEPES, 1 mM Ascorbic acid, 0.01 mM pargyline HCl and 10 mM glucose (pH 7.4) and centrifuged for 15 minutes at 25000×g. The final pellet was resuspended in perfusion buffer and placed in a water bath (37° C.) for 10 minutes. Radiolabeled neurotransmitter is added (30 uL $^3$H DA) to achieve a final concentration of 100 nM, vortexed and placed in a water bath for additional 10 minutes. Tissue-loaded filters is placed onto 11-mm diameter Gelman A/E filters on an open-air support. After a 10-minute wash period, fractions are collected to establish the basal release and agonist applied in the perfusion stream. Further fractions were collected after agonist application to re-establish the baseline. The perfusate was collected directly into scintillation vials and released radioactivity was quantified using conventional liquid scintillation techniques. Release of neurotransmitter was determined in the presence of 10 uM of various ligands and was expressed as a percentage of release obtained with a concentration of 10 uM (S)-(−)-nicotine.

Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ val-

Example 1

Sample No. 1 is (1S,4S)-(5-bromo-3-pyridyl)-2,5-diazabicyclo[2.2.1]heptane, which was prepared in accordance with the following techniques

(1S,4S)-(5-Bromo-3-pyridyl)-2-N-(tert-butoxycarbonyl)-2,5-diazabicyclo[2.2.1]heptane

(1S,4S)-3-[(N5tert-Butoxycarbonyl)-(2,5-diazabicyclo[2.2.1]heptyl)]-5-bromopyridine In a sealed pressure tube under a argon atmosphere, 3,5-dibromopyridine (0.74 g, 3.0 mmol), (1S,4S)-N-(tert-butoxycarbonyl)-2,5-diazabicyclo[2.2.1]heptane (Aldrich Chemical Company) (0.48 g, 2.3 mmol), tris(dibenzylideneacetone)dipalladium(0) (0.044 g, 0.048 mmol, 2,2'-bis(diphenylphosphino)-1,1'-binapthyl (0.058 g, 0.093 mmol), sodium tert-butoxide (0.75 g, 7.81 mmol) and toluene (15 mL) was stirred at 25° C. for 48 h. The reaction mixture was dissolved in saturated aqueous sodium chloride solution (30 mL) and the n extracted with diethyl ether (3×25 mL). The combined diethyl ether extracts were dried (Na$_2$SO$_4$), filtered and concentrated to a brown oil (1.1 g). Chromatography on silica gel using chloroform:methanol::triethylamine (30:1:1) provided pure product as a brown oil 0.81g, (94%).

(1S,4S)-(5-Bromo-3-pyridyl)-2,5-diazabicyclo[2.2.1]heptane

To a stirred solution (1S,4S)-(5-bromo-3-pyridyl)-2-N-(tert-butoxycarbonyl)-2,5-diazabicyclo[2.2.1]heptane (0.81 g, 2.29 mmol) was added 48% hydrobromic acid (15 mL). After 3 h at 25° C. the solution was concentrated to afford (0.77 g, 95%) of a brown oil. The oil was dissolved in saturated sodium chloride solution (10 mL), then stirred with 10% aqueous sodium hydroxide solution (6 mL) for 0.5 h. The mixture was extracted with chloroform (4×50 mL). The combined chloroform extracts were dried (Na$_2$SO$_4$), and concentrated under vacuum to give a brown oil (0.56 g, 97%). The material was used without further purification.

Sample No. 1 exhibits a Ki of 56 nM. The low binding constant indicates that the compound exhibits desired high affinity binding to certain CNS nicotinic receptors. Sample No. 1 exhibits an E$_{max}$ value of 36% for dopamine release, indicating that the compound is effective in eliciting neurotransmitter release.

Sample No. 1 exhibits an E$_{max}$ of 0% (at a concentration of 100 uM) at muscle-type receptors, indicating that the compound does not significantly induce activation of muscle-type receptors. The sample exhibits an E$_{max}$ of 5% (at a concentration of 100 uM) at ganglionic-type receptors. The compound has the capability to bind to human CNS receptors without activating muscle-type and ganglionic-type nicotinic acetylcholine receptors to any significant degree. Thus, there is provided a window for utilization as therapeutic agents for CNS and non-CNS disorders.

Example 2

Sample No. 2 (1S,4S)-(5-(4-methoxyphenoxy)-3-pyridyl)-2,5-diazabicyclo[2.2.1]heptane hemigalactarate, which was prepared in accordance with the following techniques

3-Bromo-5-(4-methoxyphenoxy)pyridine

To a stirred suspension sodium hydride (3.0 g of 80% in mineral oil, 100 mmol) in DMF (95 mL) in an ice water bath, 4-methoxyphenol (12.2 g, 96 mmol) was added slowly under a nitrogen atmosphere. The resulting mixture was warmed to ambient temperature and stirred for 1 h. 3,5-Dibromopyridine (15.6 g of 98%, 65 mmol) was added and the mixture was then heated at 85° C. (bath temperature) for 32 h. The mixture was cooled, diluted with water (120 mL), poured into 5N sodium hydroxide (15 mL), and extracted with ether (3×150 mL). The combined ether extracts were dried (Na$_2$SO$_4$), filtered and concentrated by rotary evaporation, to give a light yellow oil (21.9 g). The oil was diluted with ethanol and rotary evaporated (twice) to remove residual DMF and then diluted with ether (50 mL) and suction filtered to remove un-reacted 3,5-dibromopyridine. Rotary evaporation and high vacuum treatment left a lard-like product weighing 12.8 g. The product was 94% pure by GC-MS analysis, (66% yield) and was sometimes used, without further purification, in subsequent reactions. When desired, further purification (to 99.4%) was accomplished by column chromatography on Merck silica gel 60 (70–230 mesh) with 85:5:5:0.5 hexane/chloroform/ethyl acetate/methanol/aqueous ammonia.

(1S,4S)-2-(5-(4-Methoxyphenoxy)-3-pyridyl)-5-(tert-butoxycarbonyl)-2,5-diazabicyclo[2.2.1]heptane In a sealed pressure tube under a argon atmosphere, 3-bromo-5-(4-methoxyphenoxy)pyridine (2.37 g, 1.20 mmol), (1S,4S)-N-(tert-butoxycarbonyl)-2,5-diazabicyclo[2.2.1]heptane (0.21 g, 1.00 mmol), tris(dibenzylideneacetone)dipalladium(0) (0.02 g, 0.02 mmol, 2,2'-bis(diphenylphosphino)-1,1'-binapthyl (0.025 g, 0.04 mmol), sodium tert-butoxide (0.20 g, 2.0 mmol) and toluene (12 mL) was stirred at 80° C. for 24 h. The reaction mixture was dissolved in saturated aqueous sodium chloride solution (20 mL) and then extracted with diethyl ether (3×30 mL). The combined diethyl ether extracts were washed with saturated aqueous sodium chloride solution (20 mL), dried (Na$_2$SO$_4$), filtered and concentrated to a brown oil (0.37 g, 93%). The material was used without further purification.

(1S,4S)-2-(5-(4-Methoxyphenoxy)-3-pyridyl)-2,5-diazabicyclo[2.2.1]heptane

To a stirred solution (1S,4S)-(5-(4-methoxyphenoxy)-3-pyridyl)-2-N-(tert-butoxycarbonyl)-2,5-diazabicyclo[2.2.1]heptane (0.37 g, 0.932 mmol) in anisole (3.0 mL) at 0–5° C. and under a nitrogen atmosphere, trifluoroacetic acid (2.0 mL) was added drop-wise over a 10 min period. After 0.5 h at 0–5° C. the solution was adjusted to pH 5 using 10% NaOH, followed by extraction with diethyl ether (1×10 mL). The aqueous portion was adjusted to pH 11 using 10% NaOH, followed by extraction with diethyl ether (3×25 mL). The combined diethyl ether extracts were dried (Na$_2$SO$_4$), and concentrated under vacuum to give a yellow oil (0.26 g, 94%). The material was used without further purification.

(1S,4S)-(5-(4-Methoxyphenoxy)-3-pyridyl)-2-N-(tert-butoxycarbonyl)-2,5-diazabicyclo[2.2.1]heptane hemigalactarate A solution of (1S,4S)-(5-(4-methoxyphenoxy)-3-pyridyl)-2-N-(tert-butoxycarbonyl)-2,5-diazabicyclo[2.2.1]heptane (0.26 g, 0.87 mmol) in ethanol (2 mL) and water (2 mL) was heated at 60° C. as mucic acid (0.075 g, 0.0574 mmol) was added. The mixture was heated for 30 min then filtered through glass wool and concentrated to approximately 1 mL. The solution was treated with diethyl ether (4 mL). The resulting precipitate was collected, washed with diethyl ether (1 mL) and dried at 45° C. for 4 h. to afford (0.195 g, 68%) of white solid, mp 172–182° C. (d).

Sample No. 2 exhibits a Ki of 13 nM. The low binding constant indicates that the compound exhibits good high affinity binding to certain CNS nicotinic receptors. Sample No. 2 exhibits an $E_{max}$ value of 24% for dopamine release, indicating that the compound is selective in elicited neurotransmitter release. Sample No. 2 exhibits an $E_{max}$ of 12% (at a concentration of 100 uM) at muscle-type receptors, indicating that the compound does not significantly induce activation of muscle-type receptors. The sample exhibits an $E_{max}$ of 11% (at a concentration of 100 uM) at ganglionic-type receptors. The compound has the capability to bind to human CNS receptors without activating muscle-type and ganglionic-type nicotinic acetylcholine receptors to any significant degree. Thus, there is provided a window for utilization as therapeutic agents for CNS and non-CNS disorders.

Example 3

Sample No. 3 is (1S,4S)-(5-pyrimidinyl)-2,5-diazabicyclo[2.2.1]heptane hemigalactarate, which was prepared in accordance with the following techniques (1S,4S)-(5-Pyrimidinyl)-2-(N-tert-butoxycarbonyl)-2,5-diazabicyclo[2.2.1]heptane In a sealed pressure tube under a argon atmosphere, 5-bromopyrimidine (0.285 g, 1.76 mmol), (1S,4S)-N-(tert-butoxycarbonyl)-2,5-diazabicyclo[2.2.1]heptane (0.30 g, 1.44 mmol), tris(dibenzylideneacetone)dipalladium(0) (0.026 g, 0.029 mmol, 2,2'-bis(diphenylphosphino)-1,1'-binapthyl (0.037 g, 0.058 mmol), sodium tert-butoxide (0.20 g, 2.02 mmol) and toluene (15 mL) was stirred at 70° C. for 24 h. The reaction mixture was dissolved in water (30 mL) and then extracted with diethyl ether (3×30 mL). The combined diethyl ether extracts were dried ($Na_2SO_4$), filtered and concentrated to a yellow oil (0.44 g, 90%). The material was used without further purification.

(1S,4S)-(5-Pyrimidinyl)-2,5-diazabicyclo[2.2.1]heptane

To a stirred solution (1S,4S)-(5-pyrimidinyl)-2-(N-tert-butoxycarbonyl)-2,5-diazabicyclo[2.2.1]heptane (0.44 g, 1.40 mmol) in anisole (3.4 mL) at 0–5° C. and under a nitrogen atmosphere, trifluoroacetic acid (2.18 mL, 28.0 mmol) was added drop-wise over a 10 min period. After 0.75 h at 0–5° C. the solution was adjusted to pH 5 using 10% NaOH, followed by extraction with diethyl ether (1×15 mL). The aqueous portion was adjusted to pH 11 using 10% NaOH, followed by extraction with diethyl ether (3×20 mL). The combined diethyl ether extracts were dried ($Na_2SO_4$), and concentrated under vacuum to give a yellow oil (0.1580 g, 61%). The material was used without further purification.

(1S,4S)-(5-Pyrimidinyl)-2,5-diazabicyclo[2.2.1]heptane hemigalactarate

A solution of (1S,4S)-(5-pyrimidinyl)-2,5-diazabicyclo[2.2.1]heptane (0.15 g, 0.851 mmol) in methanol (3 mL) and water (3 mL) was heated at 60° C. as mucic acid (0.09 g, 0.425 mmol) was added. The mixture was heated for 30 min. then filtered through glass wool and concentrated to approximately 1 mL. The treated with diethyl ether (5 mL), then the precipitate was collected, washed with diethyl ether (1 mL) and dried at 45° C. for 4 h to afford (0.142 g, 59%) of white solid, mp 152–172° C. (d).

Sample No. 3 exhibits a Ki of 6 nM. The low binding constant indicates that the compound exhibits good high affinity binding to certain CNS nicotinic receptors. Sample No. 1 exhibits an $E_{max}$ value of 126% for dopamine release, indicating that the compound is selective in elicited neurotransmitter release.

Sample No. 3 exhibits an $E_{max}$ of 100% (at a concentration of 100 uM) at muscle-type receptors, indicating that the compound does not significantly induce activation of muscle-type receptors. The sample exhibits an $E_{max}$ of 11% (at a concentration of 100 uM) at ganglionic-type receptors. The compound has the capability to bind to human CNS receptors without activating muscle-type and ganglionic-type nicotinic acetylcholine receptors to any significant degree. Thus, there is provided a window for utilization as therapeutic agents for CNS and non-CNS disorders Example 4

Sample No. 4 is (1S,4S)-(6-chloro-3-pyridazinyl)-2,5-diazabicyclo[2.2.1]heptane hemigalactarate, which was prepared in accordance with the following techniques (1S,4S)-(6-Chloro-3-pyridazinyl)-2,5-diazabicyclo[2.2.1]heptane (1S,4S)-3-[(N-tert-butoxycarbonyl)-(2,5-diazabicyclo[2.2.1]heptyl)]-6-chloropyridazine In a sealed pressure tube under a argon atmosphere, 3,6-dichloropyridazine (0.27 g, 1.76 mmol), (1S,4S)-N-(tert-butoxycarbonyl)-2,5-diazabicyclo[2.2.1]heptane (0.30 g, 1.44 mmol), tris(dibenzylideneacetone)dipalladium(0) (0.026 g, 0.029 mmol, 2,2'-bis(diphenylphosphino)-1,1'-binapthyl (0.037 g, 0.058 mmol), sodium tert-butoxide (0.20 g, 2.02 mmol) and toluene (15 mL) was stirred at 25° C. for 24 h. The reaction mixture was dissolved in water (30 mL) and then extracted with diethyl ether (3×30 mL). The combined diethyl ether extracts were dried ($Na_2SO_4$), filtered and concentrated to a brown oil (0.41 g, 75%). The material was used without further purification.

(1S,4S)-3-[2,5-Diazabicyclo[2.2.1]heptyl)]-6-chloropyridazine

To a stirred solution of (1S,4S)-3-[(N-tert-butoxycarbonyl)-(2,5-diazabicyclo[2.2.1]heptyl)]-6-chloropyridazine (0.41 g, 1.32 mmol) in anisole (2.75 mL) at 0–5° C. and under a nitrogen atmosphere, trifluoroacetic acid (1.95 mL, 25 mmol) was added drop-wise over a 10 min period. After 0.75 h at 0–5° C. the solution was adjusted to pH 5 using 10% NaOH, followed by extraction with diethyl ether (1×15 mL). The aqueous portion was adjusted to pH 11 using 10% NaOH, followed by extraction with diethyl ether (3×20 mL). The combined diethyl ether extracts were dried ($Na_2SO_4$), and concentrated under vacuum to give a yellow oil (0.180 g, 65%). The material was used without further purification.

(1S,4S)-3-[2,5-Diazabicyclo[2.2.1]heptyl)]-6-chloropyridazine hemigalactarate

A solution of (1S,4S)-3-[2,5-diazabicyclo[2.2.1]heptyl)]-6-chloropyridazine (0.18 g, 0.850 mmol) in methanol (3 mL) and water (3 mL) was heated at 60° C. as mucic acid (0.09 g, 0.425 mmol) was added. The mixture was heated for 30 min. then filtered through glass wool and concentrated to approximately 1 mL. The solution was treated with diethyl ether (5 mL). The precipitate was collected, washed with diethyl ether (1 mL) and dried at 45° C. for 4 h to afford (0.176 g, 65%) of white solid, mp 184–194° C. (d).

Sample No. 4 exhibits a Ki of 43 nM. The low binding constant indicates that the compound exhibits good high affinity binding to certain CNS nicotinic receptors. Sample No. 4 exhibits an $E_{max}$ value of 128% for dopamine release, indicating that the compound is selective in elicited neurotransmitter release.

Sample No. 4 exhibits an $E_{max}$ of 0% (at a concentration of 100 uM) at muscle-type receptors, indicating that the compound does not significantly induce activation of muscle-type receptors. The sample exhibits an $E_{max}$ of 28% (at a concentration of 100 uM) at ganglionic-type receptors. The compound has the capability to bind to human CNS receptors without activating muscle-type and ganglionic-type nicotinic acetylcholine receptors to any significant degree Thus, there is provided a therapeutic window for utilization in the treatment of CNS disorders.

That which is claimed:

1. A compound of the formula:

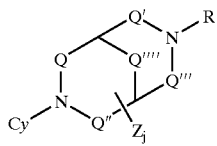

wherein Q is $(CH_2)_u$, Q' is $(CH_2)_v$, Q" is $(CH_2)_x$, Q''' is $(CH_2)_x$, and Q"" is $(CH_2)_y$ where u, v, w and x are individually 0, 1, 2, 3 or 4 and y is 1 or 2, j is from 1 to 10, R is hydrogen or lower alkyl, Cy is an aromatic ring of the formula

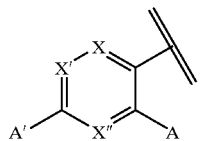

wherein X and X' are nitrogen and X" is nitrogen bonded to oxygen, or carbon bonded to a substituent species, and Z, A and A' are, independently, hydrogen or a non-hydrogen substituent species selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_q$OR', —OC(=O)R', —(CR'R")$_q$OCH$_2$C$_2$R', —(CR'R")$_q$C(=O)R', —O(CR'R")$_q$C(=O)R', —C$_2$(CR'R")$_q$OR', —(CR'R")$_q$NR'R", —OC(=O)NR'R" and —NR'C(=O)OR' where R' and R" are individually hydrogen or lower alkyl, an aromatic group-containing species or a substituted aromatic group-containing species, and q is an integer from 1 to 6, wherein the compound is a 2.2.1 bicycloheptane, wherein the aromatic group containing species is selected from the group consisting of pyridinyl, quinolidinyl, pyrimidinyl, phenyl, substituted phenyl and benzyl, and wherein the term substituted refers to the same list of substitutents described above with respect to A and A'.

2. The compound of claim 1, wherein j is 1 or 2.

3. A compound selected from the group consisting of (1S,4S)-2-(3pyridyl)-2,5-diazabicyclo[2.2.1]heptane, (1S,4S)-2-(5-(4-methoxyphenoxy)-3-pyridyl)-2,5-diazabicyclo[2.2.1]heptane, (1S,4S)-2-(5-pyrimidinyl)-2,5-diazabicyclo[2.2.1]heptane and (1S,4S)-2-(6-chloro-3-pyridazinyl)-2,5-diazabicyclo[2.2.1]heptane.

4. The pharmaceutical composition incorporating a carrier and a compound of the formula

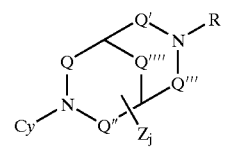

wherein Q is $(CH_2)_u$, Q' is $(CH_2)_y$, Q" is $(CH_2)_x$, Q''' is $(CH_2)_x$, and Q"" is $(CH_2)_y$ where u, v, w and x are individually 0, 1, 2, 3 or 4 ad y is 1 or 2, j is from 1 to 10, R is hydrogen or lower alkyl, Cy is an aromatic ring of the formula

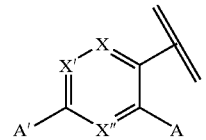

wherein X and X' are nitrogen and X" is nitrogen, nitrogen bonded to oxygen, or carbon bonded to a substituent species, and Z, A and A' are, independently, hydrogen or a non-hydrogen substituent species selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —(=O)NR'R", —NR'C(=O)R', —C(=O)R', —C(=O)OR', —(CH$_2$)$_q$OR', —OC(=O)R', —(CR'R")$_q$OCH$_2$C$_2$R', —(CR'R")$_4$C(=O)R', —O(CR'R")$_q$C(=O)R', —C$_2$(CR'R")$_q$OR', —(CR'R")$_q$NR'R", —OC(=O)NR'R"and —NR'C(=O)OR' where R' and R" are individually hydrogen or lower alkyl, an aromatic group-containing species or a substituted aromatic group-containing species, and q is an integer from 1 to 6, and a carrier, wherein the compound is a 2.2.1 bicycloheptane, wherein the aromatic group containing species is selected from the group consisting of pyridinyl, quinolidinyl, pyrimidinyl, phenyl, substituted phenyl and benzyl, and wherein the term substituted refers to the same list of substituents described above with respect to A and A'.

5. The pharmaceutical composition of claim 4, wherein j is 1 or 2.

6. A pharmaceutical composition including a carrier and a compound selected from the group consisting of (1S,4S)-2-(3-pyridyl)-2,5-diazabicyclo[2.2.1]heptane, (1S,4S)-2-(5-(4-methoxyphenoxy)-3-pyridyl)-2,5-diazabicyclo[2.2.1]heptane, (1S,4S)-2-(5-pyrimidinyl)-2,5-diazabicyclo[2.2.1]heptane and (1S,4S)-2-(6-chloro-3-pyridazinyl)-2,5-diazabicyclo[2.2.1]heptane.

7. A compound of the formula:

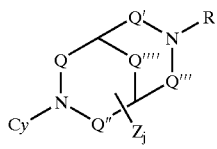

wherein Q is $(CH_2)_u$, Q' is $(CH_2)_v$, Q" is $(CH_2)_x$, Q'" is $(CH_2)_y$ and Q"" is $(CH_2)_y$ where u, v, w and x are individually 0, 1, 2, 3 or 4 and y is 1 or 2, j is from 1 to 10, R is hydrogen or lower alkyl, Cy is an aromatic ring of the formula

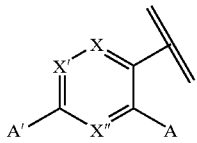

wherein X' and X" are nitrogen and X is nitrogen, nitrogen bonded to oxygen, or carbon bonded to a substituent species, and Z, A and A' are, independently, hydrogen or a non-hydrogen substituent species selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_q$OR', —OC(=O)R', —(CR'R")$_q$OCH$_2$C$_2$R', —(CR'R")$_q$C(=O)R', O(CR'R")$_q$C(=O)R', —C$_2$(CR'R")$_q$OR', —(CR'R")$_q$NR'R", —OC(=O)NR'R" and —NR'C(=O)OR' where R' and R" are individually hydrogen or lower alkyl, an aromatic group-containing species or a substituted aromatic group-containing species, and q is an integer from 1 to 6, wherein the compound is a 2.2.1 bicycloheptane.

wherein the aromatic group containing species is selected from the group consisting of pyridinyl, quinolidinyl, pyrimidinyl, phenyl, substituted phenyl and benzyl, and wherein the term substituted refers to the same list of substituents described above with respect to A and A'.

8. The compound of claim 7 wherein j is 1 or 2.

9. A pharmaceutical composition comprising a carrier and a compound as claimed in claim 7.

10. The pharmaceutical composition of claim 9, wherein j is 1 or 2.

* * * * *

Adverse Decision In Interference

Patent No. 6,440,970, Thomas Jeffrey Clark, PHARMACEUTICAL COMPOSITIONS AND METHODS FOR USE, Interference No. 105,368, final judgment adverse to the patentees rendered, April 6, 2006, as to claims 1-10.

*(Official Gazette September 19, 2006)*